(12) United States Patent
Tsai (10) Patent No.: US 6,421,898 B1
(45) Date of Patent: Jul. 23, 2002

(54) DEVICE FOR SEPARATING A NEEDLE FROM A USED SYRINGE

(76) Inventor: David Tsai, No. 113-9, Gin-Chen Street, Chang Hua City (TW)

( * ) Notice: Subject to any disclaimer, the term of this patent is extended or adjusted under 35 U.S.C. 154(b) by 0 days.

(21) Appl. No.: 09/833,379

(22) Filed: Apr. 12, 2001

(51) Int. Cl.[7] .............................................. B23P 19/04
(52) U.S. Cl. ........................ 29/239; 29/283.5; 29/280; 29/282
(58) Field of Search ...................... 29/239, 816, 283.5, 29/280, 282

(56) References Cited

U.S. PATENT DOCUMENTS

| | | | | |
|---|---|---|---|---|
| 4,255,996 A | * | 3/1981 | Choksi et al. ................. | 83/140 |
| 4,466,538 A | * | 8/1984 | Gianni ......................... | 206/366 |
| 4,576,281 A | * | 3/1986 | Kirksey ....................... | 206/370 |
| 4,802,579 A | * | 2/1989 | Hall et al. ..................... | 29/239 |
| 4,917,243 A | * | 4/1990 | Abram et al. ................ | 206/365 |
| 4,956,907 A | * | 9/1990 | Bruno ......................... | 29/426.5 |
| 5,623,762 A | * | 4/1997 | White .......................... | 29/816 |

* cited by examiner

Primary Examiner—Joseph J. Hail, III
Assistant Examiner—Lee Wilson
(74) Attorney, Agent, or Firm—Alan Kamrath; Rider, Bennett, Egan & Arundel, LLP (57) ABSTRACT

A device separates a needle from a syringe before subsequent separate handling of the needle and the rest of the syringe. The needles are accumulated in a container made of stainless steel which is then put into a smelting furnace, thereby preventing the worker from being pricked and thus infected by the used needles. The plastic portions of the syringes are accumulated in another container for further handling.

20 Claims, 9 Drawing Sheets

DEVICE FOR SEPARATING A NEEDLE FROM A USED SYRINGE

BACKGROUND OF THE INVENTION

1. Field of the Invention

The present invention relates to a device for separating a needle from a used syringe, particularly a hypodermic syringe.

2. Description of the Related Art

Handling of used syringes, particularly hypodermic syringes, is a problem for hospitals and/or other medical treating or examination centers. The syringes are often accumulated and then burnt, yet the workers are exposed to the needles during manual handling. The residual of the syringes after burning cannot be recycled, as a syringe comprises a needle made of stainless steel and other parts that are made of plastics having a melting point lower than that of stainless steel.

SUMMARY OF THE INVENTION

It is the primary object of the present invention to provide a device for separating a needle from a syringe before subsequent separate handling of the needle and the rest of the syringe. The needles are accumulated in a container made of stainless steel which is then put into a smelting furnace or the like, thereby preventing the worker from being pricked and thus infected by the used needles. The plastic portions of the syringes are accumulated in another container for further handling. Thus, the device in accordance with the present invention provides a solution for used syringes, which is not only hygienic but also friendly to the environment.

In accordance with the present invention, a device for separating a needle from a used syringe comprises means for holding a used syringe and means for separating a needle from the used syringe. A container is provided for accumulating the needle separated from the used syringe. The container is made of a material identical to that of the needle. Another container is provided for accumulating the used syringe without the needle.

In an embodiment of the invention, the device includes a main body in which the holding means and the separating means are mounted. The device includes a compartment, the holding means being a groove communicated with the compartment in the main body, the groove being configured to hold a needle hub of the used syringe. The main body includes a post mounted therein. The separating means includes a shaft having a pulling member mounted thereon. The needle of the used syringe is extended through the pulling member and has a peripheral portion abutting against the post. The shaft is rotatable to bend the needle by means of pressing the needle against the post and finally pulling the needle from the needle hub. A torsion spring is provided for returning the shaft to its initial position.

The main body further includes a plate securely mounted therein. The shaft extends through the plate. A guide plate is securely attached to the plate and mounted around the shaft. The guide plate includes an arcuate groove and the shaft has a pin slidably guided in the arcuate groove such that the shaft moves axially when the shaft is turned. The bent needle impinges the plate and is thus separated from the used syringe when the shaft moves axially.

In addition, means are provided for driving the shaft. In an embodiment of the invention, the shaft includes an end on which a driven gear is mounted. The driving means comprise a driving gear rotatably supported by the main body and a manual handle mounted outside the main body and securely attached to a gear shaft of the driving gear. In an alternative embodiment, the driving means comprise a driving gear rotatably supported by the main body and a motor operably connected to the driving gear. An on/off switch is provided for controlling the motor.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
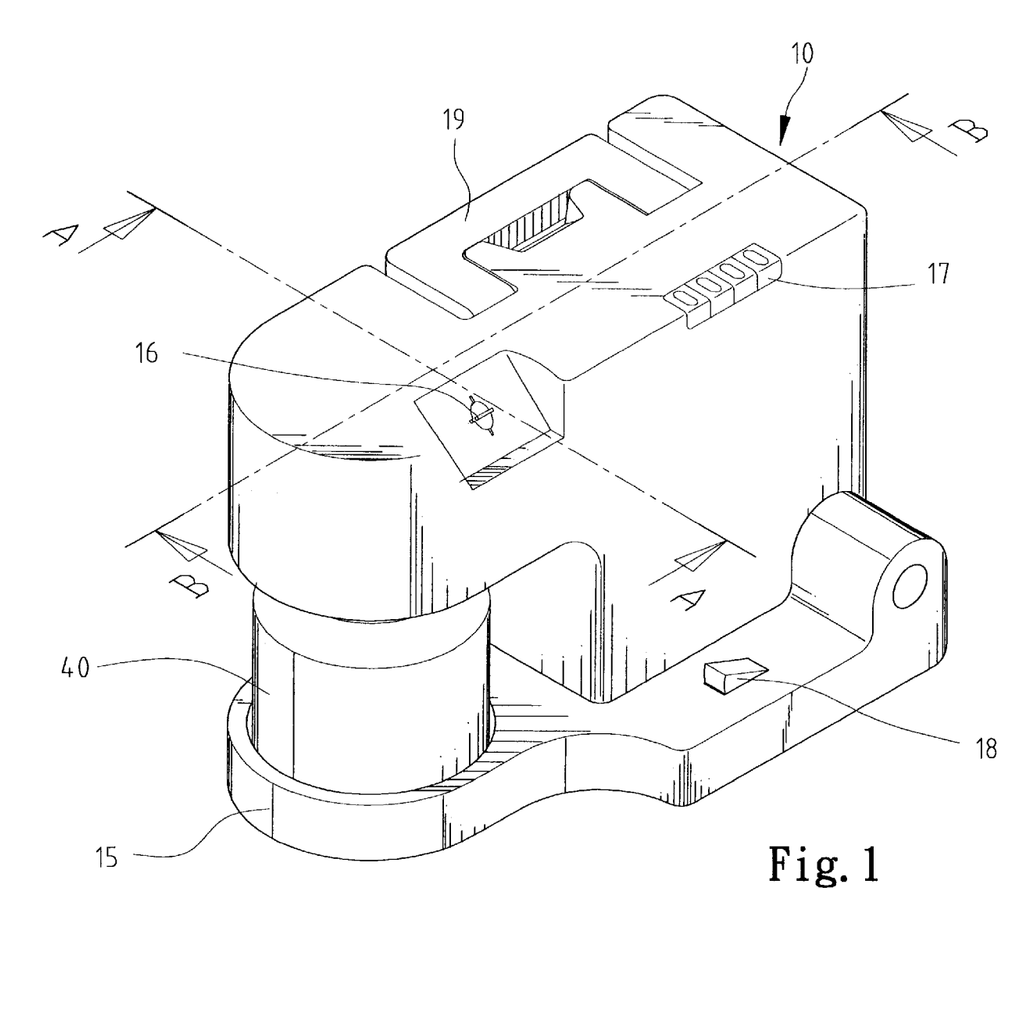
FIG. 1 is a perspective view of a device for separating a needle from a used syringe in accordance with the present invention.
Figure 2:
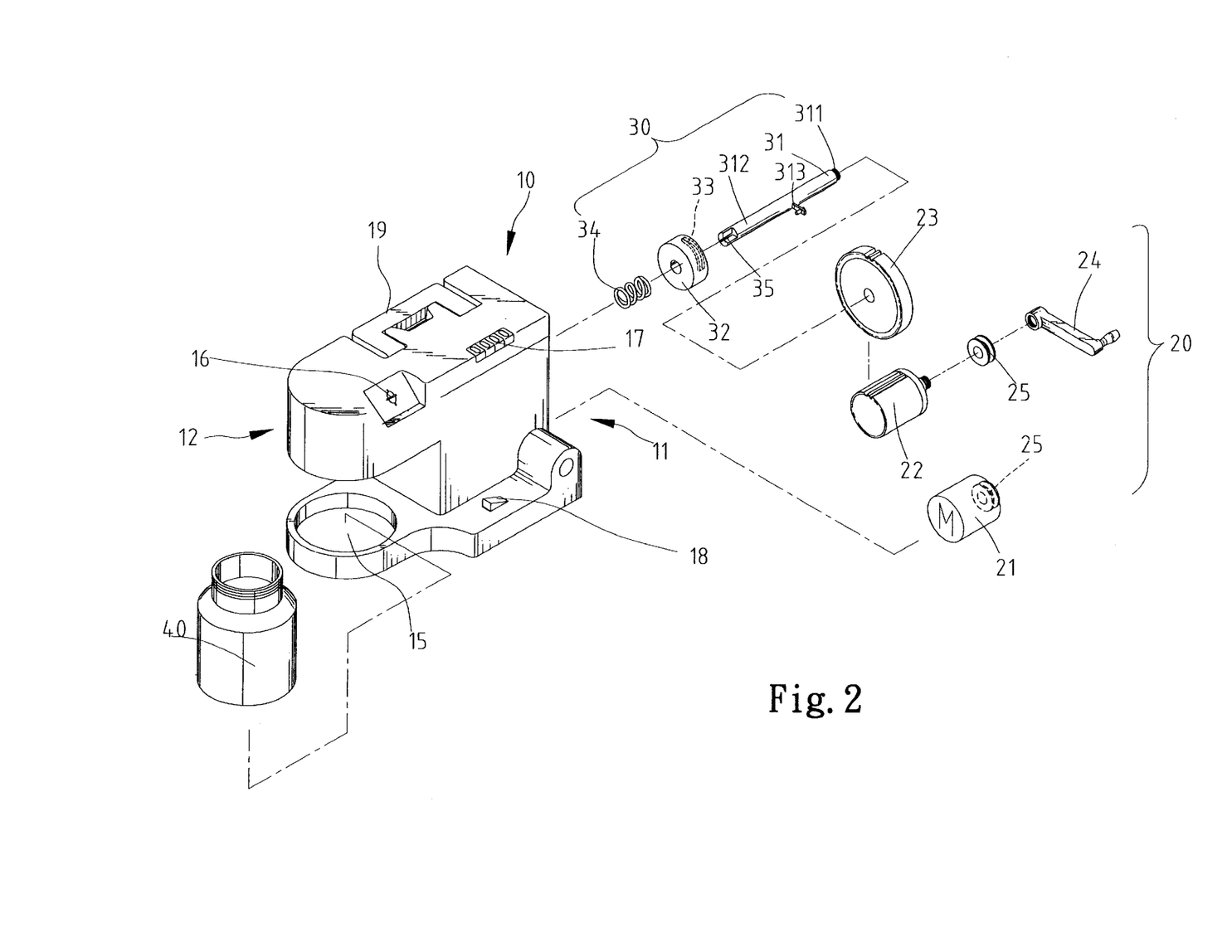
FIG. 2 is an exploded perspective view of the device in accordance with the present invention.
Figure 3:
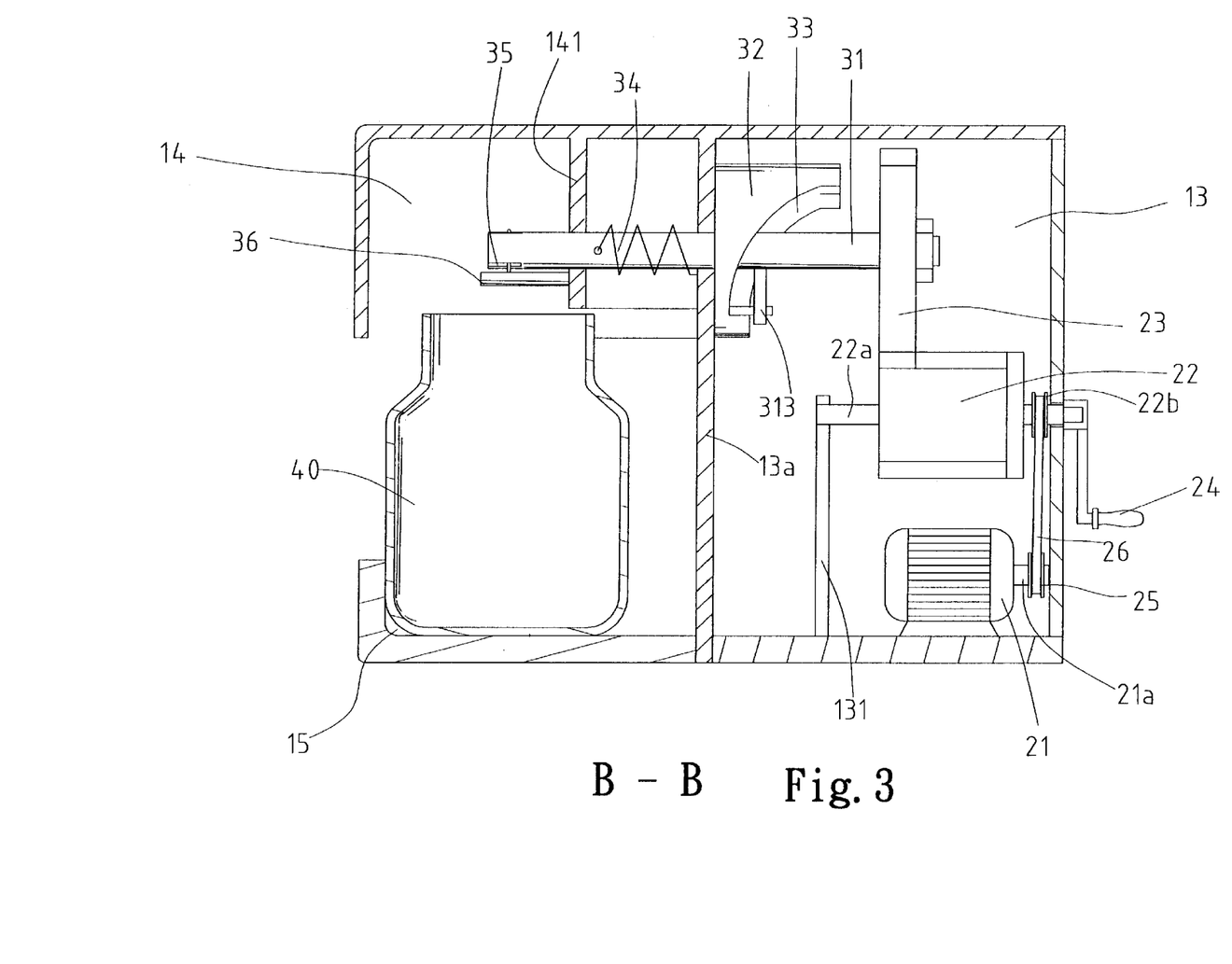
FIG. 3 is a sectional view taken along plane B—B in FIG. 1.
Figure 4:
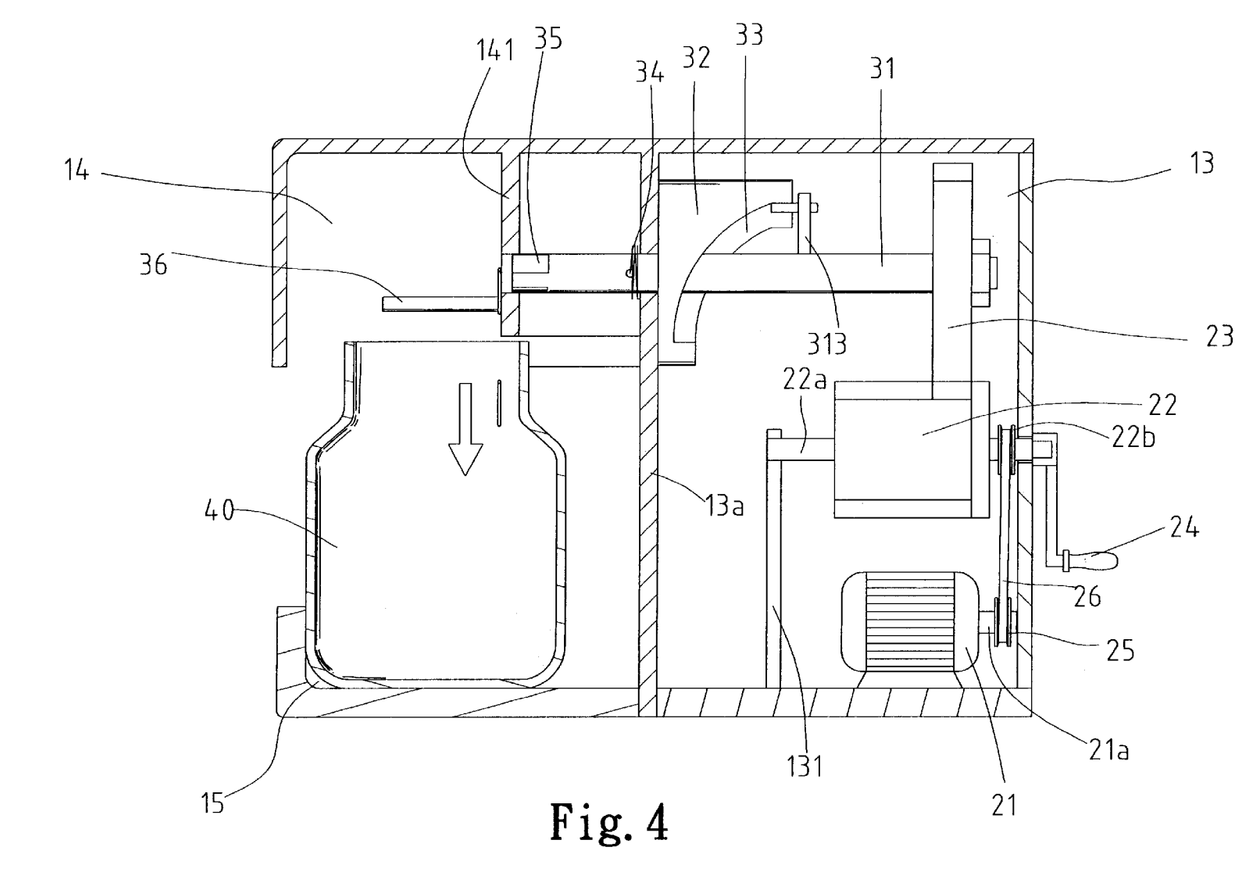
FIG. 4 is a sectional view similar to FIG. 3, illustrating separation of a needle from a used syringe.
Figure 5:
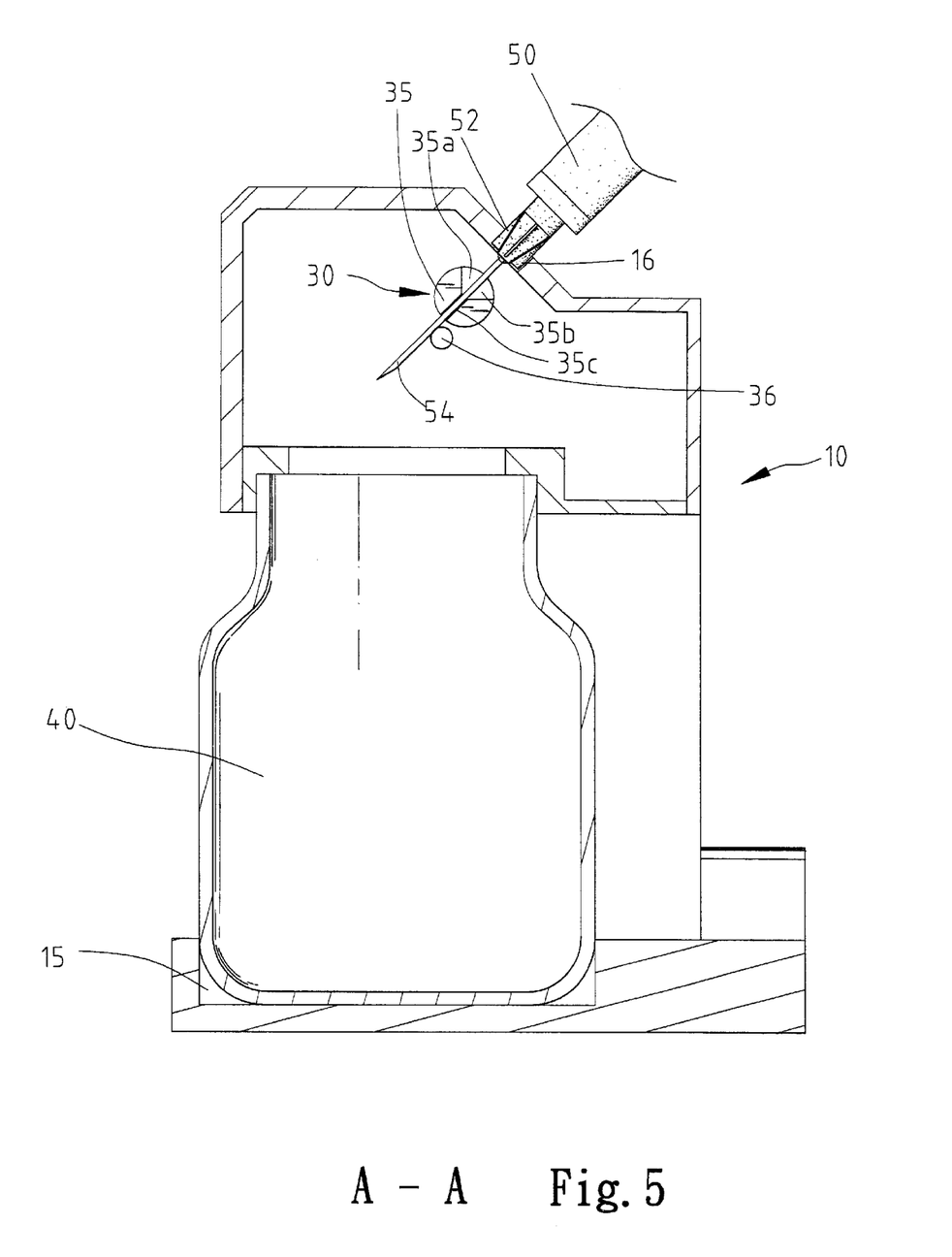
FIG. 5 is a sectional view taken along plane A—A in FIG. 1.
Figure 6:
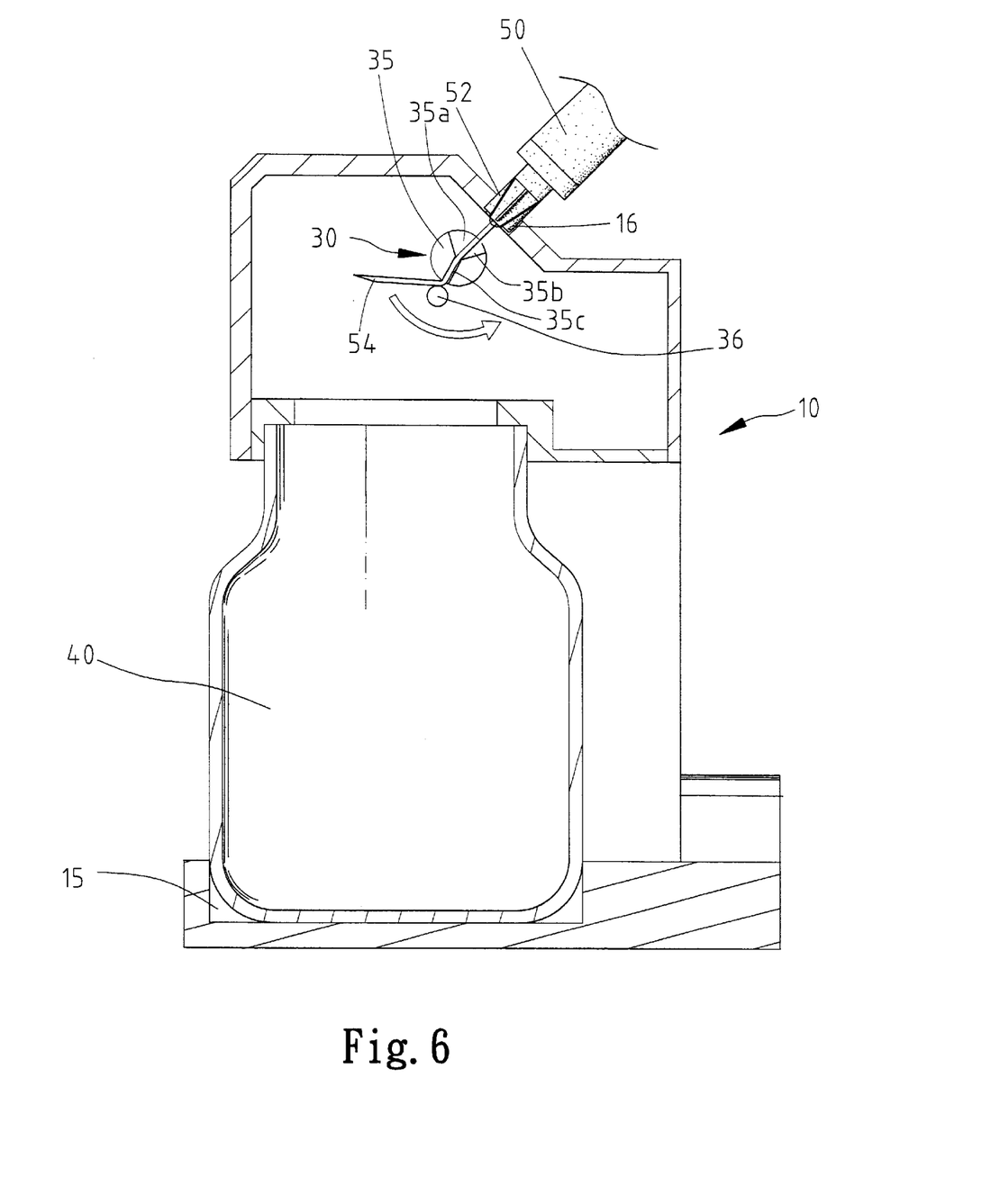
FIGS. 6 through 8 are sectional views similar to FIG. 5, illustrating separation of a needle from a used syringe.
Figure 7:
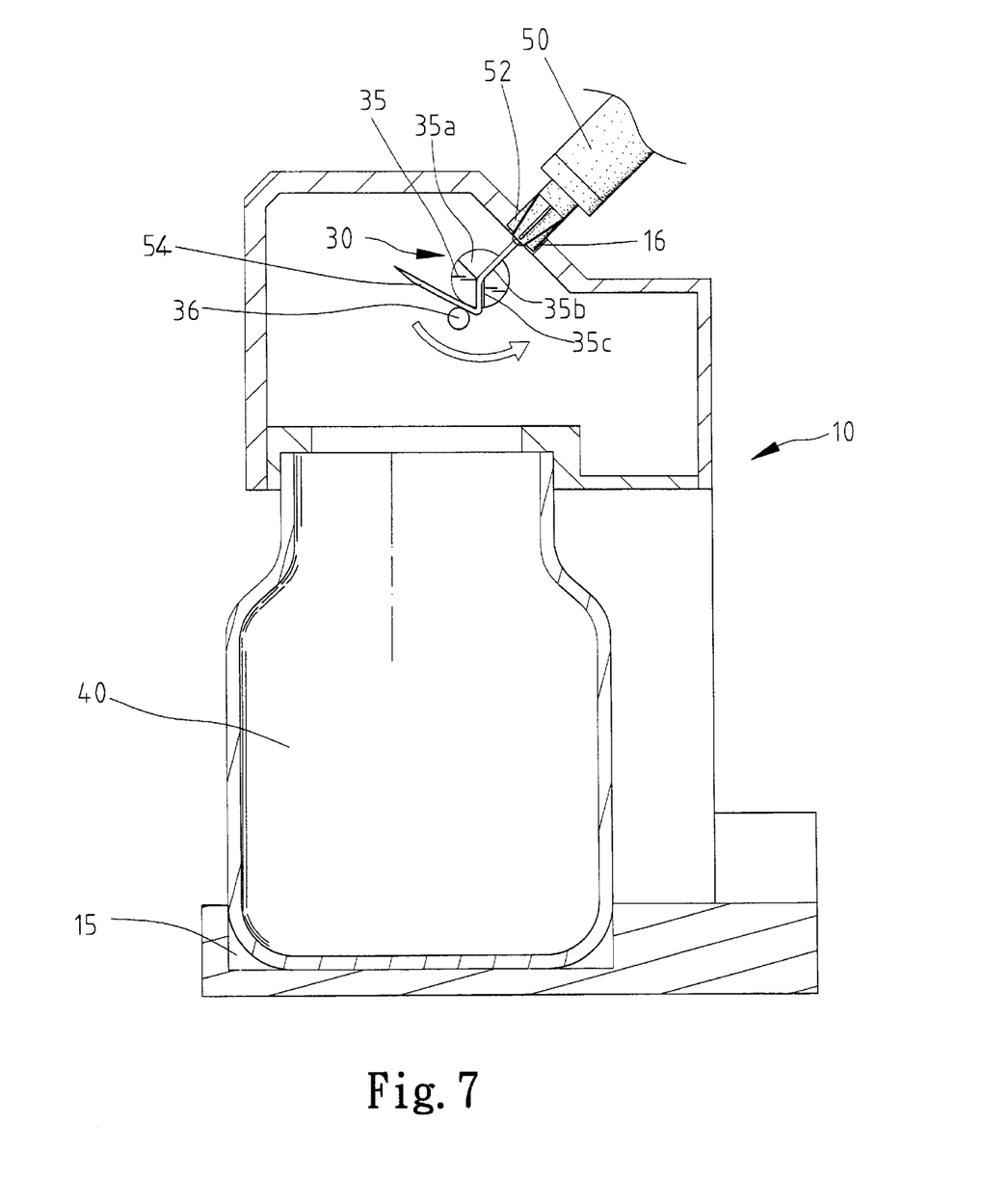

Referring to FIGS. 1 through 9 and initially to FIGS. 1 through 3, a device for separating a needle from a used syringe in accordance with the present invention generally includes a main body 10 having a first compartment 13 in a first end 11 thereof and a second compartment 14 in a second end 12 thereof. A container 40 made of stainless steel is placed in the main body 10 in a position 15 below the second compartment 14. Referring to FIGS. 1 and 5, a holding member 16 (in the form of a seat or groove that is communicated with the second compartment 14) is mounted to or formed on the second end 12 of the main body 10 for holding a needle hub 52 of a used syringe 50. The holding member 16 allows a needle 54 of the used syringe 50 to extend into the second compartment 14 and thus to be located above the container 40. A counter 17 for counting the total number of pulled needles and a switch 18 for controlling rotation of a motor 21 are mounted to the first end 11 of the main body 10. A foldable handle 19 is mounted on top of the main body 10 for easy carriage, as best shown in FIG. 1.

Still referring to FIGS. 1 through 3, a driving means 20 is mounted in the first compartment 13 for driving a separating means 30 mounted in the first compartment 13 and the second compartment 14. The driving means 20 includes the above-mentioned motor 21, a driving gear 22, a driven gear 23 meshed with the driving gear 22, and a manual handle 24 outside the main body 10. The driving gear 22 has a gear shaft 22a rotatably mounted between a positioning plate 131 in the first compartment 13 and a portion of a housing (not labeled) of the main body 10. The driving gear 22 can be driven by either the manual handle 24 that is engaged with the gear shaft 22a or the motor 21 having an output shaft 21a that is connected to the gear shaft 22a by a belt 26 and two pulleys 25 and 22b, best shown in FIG. 3.

Referring to FIGS. 2 and 3, the separating means 30 comprises a shaft 31, a guide plate 32, a torsion spring 34, and a pulling member 35. The shaft 31 includes a first end 311 in the first compartment 13 and a second end 312 in the second compartment 14. The driven gear 23 is mounted to the first end 311 of the shaft 31 to rotate therewith. The shaft 31 is extended through and thus supported by a partition plate 13a between the first compartment 13 and the second compartment 14 and a plate 141 in the second compartment 14. The guide plate 32 is securely mounted to the plate 141 and around the shaft 31 and includes an arcuate groove 33 into which a pin 313 on the shaft 31 extends. Thus, the shaft 31 moves axially under the guidance of the arcuate groove 33 when the shaft 31 is turned. The torsion spring 34 returns the shaft 31 to its initial position. The pulling member 35 is mounted on the second end 312 of the shaft 31 and includes a passage 35a having a wider, sector-like first portion 35b and a narrow, straight second portion 35c, best shown in FIG. 5. Located below the pulling member 35 and attached to the plate 141 is a post 36 for bending the needle 54 of the used syringe 50.

Figure 8:
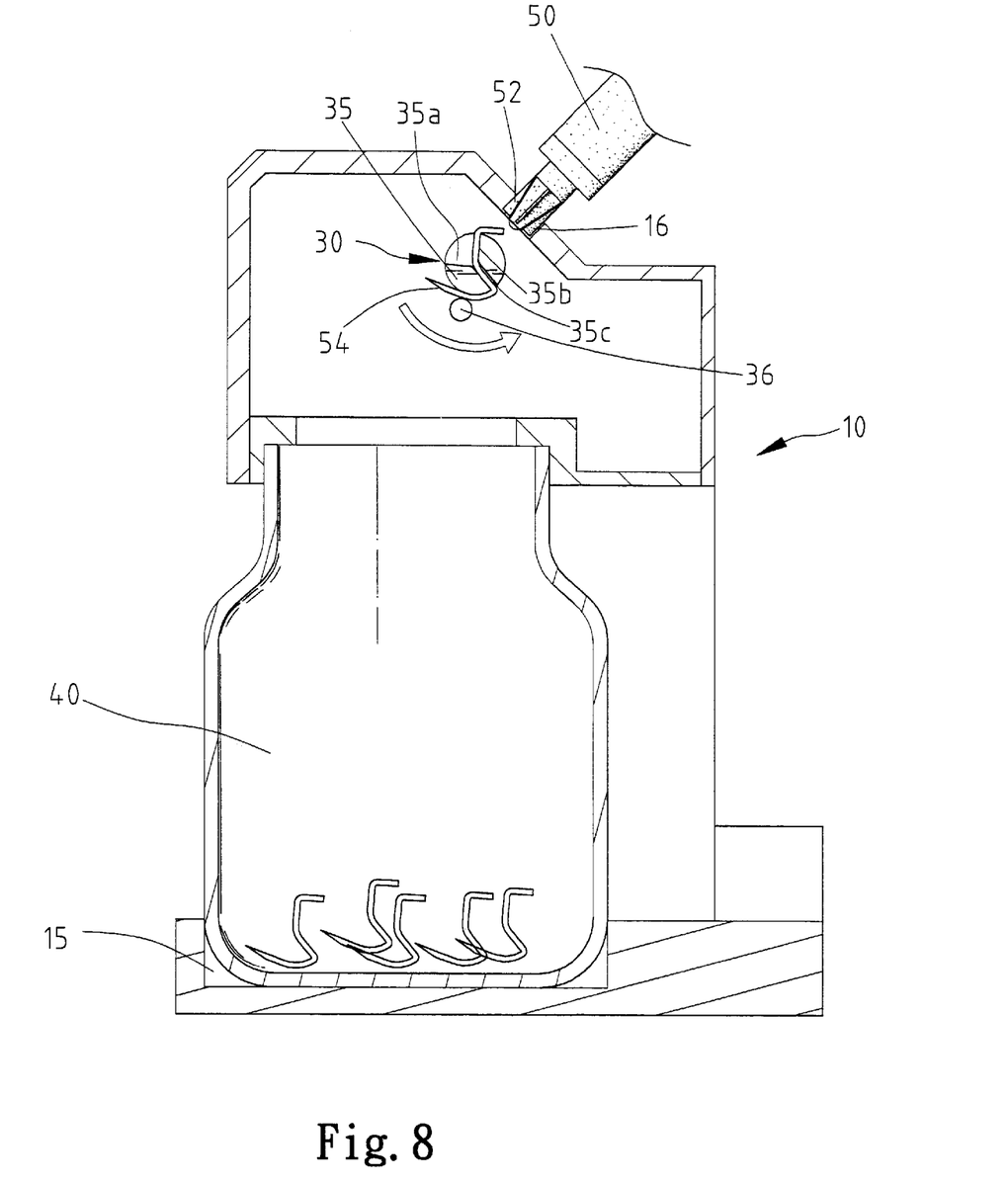
Figure 9:
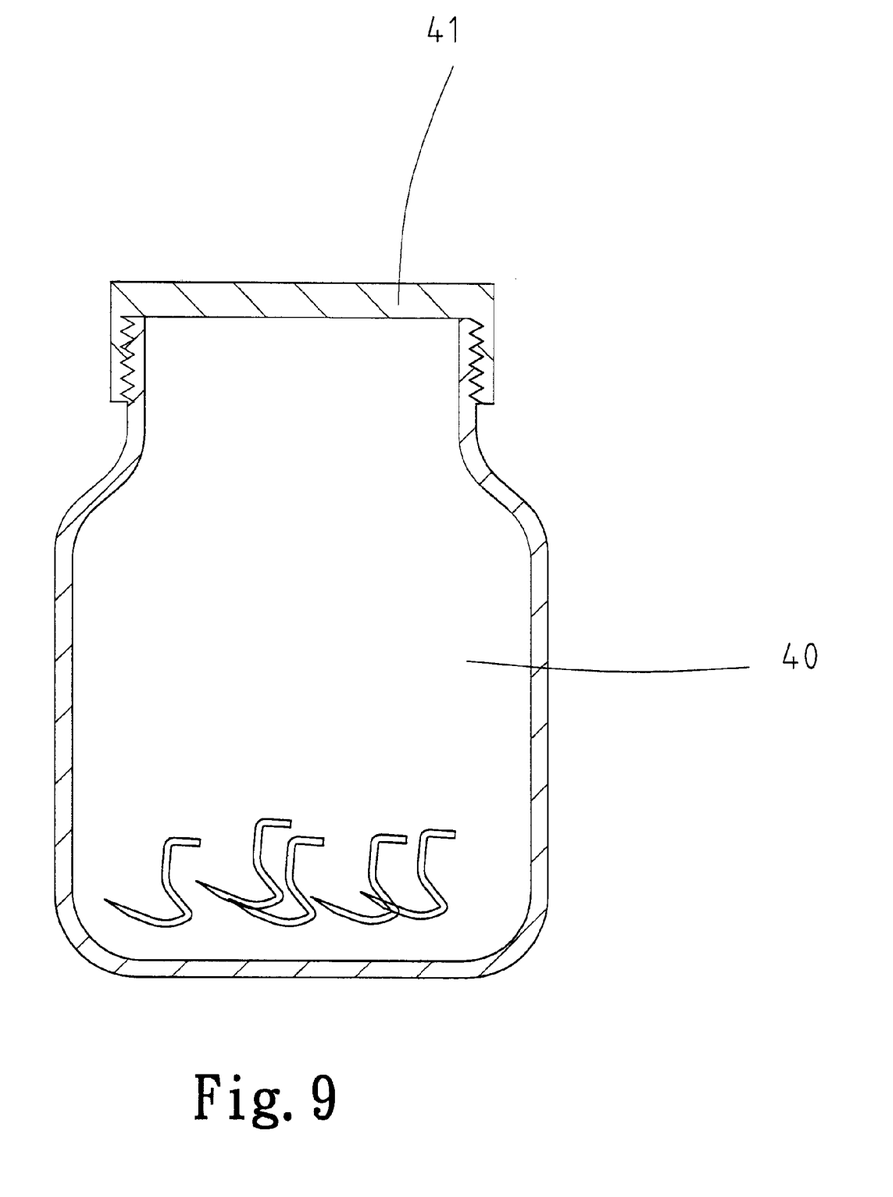
FIG. 9 is a sectional view of a container for accumulating needles.

When the driving gear 22 is rotated by means of either turning the switch 18 on or rotating the manual handle 24, the shaft 31 turns and thus bends the needle 54 (see FIGS. 6 and 7) by means of pressing the needle 54 against the post 36. Since the pin 313 is guided along the arcuate groove 33 of the guiding plate 32, the shaft 31 also moves axially away from the container 40 until the needle 54 impinges the plate 141. As a result, the needle 54 is completely separated from the needle hub 52 (FIGS. 4 and 8). After separation of the needle 54, the shaft 31 is returned to its initial position under the action of the torsion spring 34. The needles 54 separated from the used syringes 50 are accumulated in the container 40 under the guidance of the plate 141. The container 40 is then moved into a smelting furnace or the like after putting on a cover 41 to enclose the container 40. The container 40 and the needles 54 are both made of stainless steel and thus can be melted together for recycling purpose. The plastic parts of the syringes 50 are accumulated in another container (not shown) for recycling purpose.

Although the invention has been explained in relation to its preferred embodiment, it is to be understood that many other possible modifications and variations can be made without departing from the scope of the invention as hereinafter claimed.

What is claimed is:

1. A device for separating a needle extending along a longitudinal axis from a used syringe, the device comprising:
   means for holding the used syringe; and
   means for turning the needle of the used syringe about an axis not parallel to the longitudinal axis and thus separating the needle from the used syringe.

2. The device as claimed in claim 1, further comprising a container for accumulating the needle separated from the used syringe.

3. The device as claimed in claim 2, wherein the container is made of a material identical to that of the needle.

4. The device as claimed in claim 1, further comprising a container for accumulating the used syringe without the needle.

5. The device as claimed in claim 1, wherein the device includes a main body in which the holding means and the separating means are mounted.

6. The device as claimed in claim 5, wherein the device includes a compartment, the holding means being a groove communicated with the compartment in the main body, the groove being configured to hold a needle hub of the used syringe.

7. The device as claimed in claim 1 with the means for turning the needle bending the needle when separating the needle from the used syringe.

8. A device for separating a needle from a used syringe, the device comprising:
   a main body mounting means for holding the used syringe, wherein the main body includes a post mounted therein; and
   a shaft having a pulling member mounted thereon, the needle of the used syringe extending through the pulling member and having a peripheral portion abutting against the post, the shaft being rotatable to bend the needle by means of pressing the needle against the post and finally pulling the needle from the syringe.

9. The device as claimed in claim 8, further comprising means for returning the shaft to its initial position.

10. The device as claimed in claim 8, wherein the main body further includes a plate securely mounted therein, the shaft extending through the plate, further comprising a guide plate securely attached to the plate and mounted around the shaft, the guide plate including an arcuate groove, the shaft having a pin slidably guided in the arcuate groove such that the shaft moves axially when the shaft is turned, wherein the bent needle impinges the plate and is thus separated from the used syringe when the shaft moves axially.

11. The device as claimed in claim 8, further comprising means for driving the shaft.

12. The device as claimed in claim 11, wherein the shaft includes an end on which a driven gear is mounted, the driving means comprising a driving gear rotatably supported by the main body and a manual handle mounted outside the main body and securely attached to a gear shaft of the driving gear.

13. The device as claimed in claim 11, wherein the shaft includes an end on which a driven gear is mounted, the driving means comprising a driving gear rotatably supported by the main body and a motor operably connected to the driving gear.

14. The device as claimed in claim 13, further comprising a switch for controlling on and off of the motor.

15. The device as claimed in claim 8, further comprising a container for accumulating the needle separated from the used syringe.

16. The device as claimed in claim 15, wherein the container is made of a material identical to that of the needle.

17. The device as claimed in claim 8, further comprising a container for accumulating the used syringe without the needle.

18. The device as claimed in claim 8, further comprising a handle mounted on top of the main body for carriage.

19. A device for separating a needle from a used syringe, the device comprising:
   means for holding the used syringe;
   means for separating the needle from the used syringe; and
   a counter for counting a number of needles separated from the used syringes.

20. A device for separating a needle extending along a longitudinal axis from a used syringe, the device comprising:
   a main body holding the used syringe; and
   a pulling member mounted in the main body for receiving the needle of the used syringe, with the pulling member being rotatable to turn the needle about an axis not parallel to the longitudinal axis and thus separating the needle from the used syringe.

* * * * *